US00PP14896P3

(12) United States Plant Patent
Boeder

(10) Patent No.: US PP14,896 P3
(45) Date of Patent: Jun. 15, 2004

(54) CHRYSANTHEMUM PLANT NAMED 'SWING TIME DARK'

(50) Latin Name: *Dendranthema grandiflora*
Varietal Denomination: Swing Time Dark

(75) Inventor: Mark Roland Boeder, Den Haag (NL)

(73) Assignee: Cleangro Ltd., Chichester (GB)

( * ) Notice: Subject to any disclaimer, the term of this patent is extended or adjusted under 35 U.S.C. 154(b) by 161 days.

(21) Appl. No.: 09/900,239

(22) Filed: Jul. 6, 2001

(65) Prior Publication Data

US 2003/0009810 P1 Jan. 9, 2003

(51) Int. Cl.[7] ..... A01H 5/00
(52) U.S. Cl. ..... Plt./298

(58) Field of Search ..... Plt./298

(56) References Cited

PUBLICATIONS

The Plant 'Swing Time Dark' was not the subject of a printed publication or an application for plant Breeder's Rights prior to the filing date of this U.S. plant patent application. Moreover, the instant plant was not sold, offered for sale or otherwise made publicly available in the United States or elsewhere prior to the filing date of this U.S. plant patent application.

*Primary Examiner*—Bruce R. Campell
*Assistant Examiner*—Michelle Kizilkaya

(57) ABSTRACT

A new variety of Chrysanthemum plant named 'Swing Time Dark' having deep orange red bronze single type flowers and a slightly domed capitulum form and branching habit.

1 Drawing Sheet

Latin name of the genus and species: Botanical classification: *Dendranthema grandiflora.*

Variety denomination: The new Chrysanthemum variety denomination is 'Swing Time Dark.'

BACKGROUND OF THE INVENTION

The present invention comprises a new and distinct cultivar of Chrysanthemum botanically known as *Dendranthema grandiflora,* and referred to by the cultivar name 'Swing Time Dark.'

'Swing Time Dark' identified as 20230-3, was discovered as a natural mutation of a whole plant in a controlled cultivated planting of the variety 'Swing Time' (unpatented). The variety 'Swing Time Dark' has been asexually reproduced by vegetative cuttings at Chichester, West Sussex, United Kingdom and the distinguishing characteristics are retained through successive generations of asexual reproduction.

BRIEF SUMMARY OF THE INVENTION

'Swing Time Dark' is a pot type of Chrysanthemum plant variety having a slightly domed capitulum form and deep orange red bronze single flowers.

COMPARISON WITH PARENT

Plant habit of the new Chrysanthemum variety 'Swing Time Dark' is similar to the parent cultivar 'Swing Time.' In side-by-side comparisons in Chichester, West Sussex, United Kingdom, under commercial practice, plants of the new Chrysanthemum variety 'Swing Time Dark' differed from plants of the parent cultivar 'Swing Time' in the following characteristics.

1. Flowers of the new variety 'Swing Time Dark' are a more deep orange red color than 'Swing Time.'

COMPARISON WITH OTHER VARIETIES

Plants of the new Chrysanthemum variety 'Swing Time Dark' are similar to the cultivar 'Virunga Dark' (unpatented) in plant habit and growth rate. In side-by-side comparisons in Chichester, West Sussex, United Kingdom, under commercial practice, Plants of the new Chrysanthemum variety 'Swing Time Dark' compared to plants of the cultivar 'Virunga Dark' in the following characteristics.

1. The flowers of the new variety 'Swing Time Dark' are dark orange whereas the flowers of the cultivar 'Virunga Dark' are light orange.
2. The plants of the new variety 'Swing Time Dark' have smaller inflorescence than the plants of the cultivar 'Virunga Dark.'

BRIEF DESCRIPTIONS OF ILLUSTRATIONS

FIG. 1 is a whole plant view of the new variety 'Swing Time Dark' grown in a pot. The colors shown are as true as possible within the usual limits of this kind of illustration. The plant shown in the illustration is 60 days from the start of Short Days.

DETAILED BOTANICAL DESCRIPTION

The following description of the new Chrysanthemum variety 'Swing Time Dark' is of plants grown in a greenhouse in Chichester, West Sussex, United Kingdom in the month of June. The cultivar has not been observed under all possible environmental conditions. The phenotype may vary significantly with variations in the environment such as temperature, length of day and light intensity, without any variance in genotype. The commercial classification of the new variety is a pot Chrysanthemum.

Plants of the new variety have been grown successfully under temperature conditions averaging about 18° C. at night and about 24° C. to 25° C. during the day under light conditions of about [e.g., 5,000 to 6,000] foot candles. The plants respond well to the use of growth retardant, such as three B9 treatments at about 2500 ppm. To produce a commercial product the plants may be pinched once. The typical container size for commercial growth is 14 cm. It has been observed that the shelf life of the new variety is about 21 days with a response time of about 7½ weeks. The new variety is suitable for growth in a temperature range of 15° C. to 25° C.

The following description is with respect to a plant produced as a pot Chrysanthemum. In the description of this new Chrysanthemum variety, color values have been taken from The Royal Horticultural Society Colour Chart (R.H.S.C.C.).

Plant

Plant type: Pot.
Habit: Upright and branching.
Height: 24 cm.
Width: 32 cm.
Branching characteristics: Free and spreading.
Length of lateral branches: 15–20 cm.
Number of breaks from pinch: 4–6.
Stem color: Near 137B.
Response time: Near 54 days.
Vigor: Medium/tall.
Shelf life: Near 21 days.
Disease (susceptibility or resistance observed): None observed.
Pest (resistance or susceptibility): None observed.
Growth retardant type and treatment: 3 applications of 2.5 grams/litre at 2 days, 21 days and 28 days after sticking of unrooted cuttings.
The plants were grown for two weeks in Long Day conditions (20 hours of light) and then transferred to Short Day conditions (13 hours of dark).
Propagation:
*Type.*—Vegetative propagation via stem cuttings.
*Time to rooting.*—12–14 days with soil temperatures of 18° C.
*Rooting habit.*—Fine and fibrous.

Foliage

Number of leaves per lateral branch: 10–14.
Compound or single: Single.
Arrangement of leaves: Alternate.
*Shape of leaf.*—Typically 5 lobed, ovate.
*Size of leaf.*—Width (cm): near 4–6 Length (cm): near 6–8.
*Leaf apex.*—Rounded.
*Base.*—Cordate.
*Attachment.*—Petioled.
*Aspect.*—Slightly undulating.
*Margin.*—Palmately lobed.
*Surface characteristics.*—Top: pubescent. Bottom: pubescent.
Petiole:
*Color.*—Near 137C.
*Length.*—Near 2 cm.
Venation: Net prominent midvein at underside.
*Color.*—Upper side: near 137B. Under side: near 137D.
Color:
*Mature leaf, upper side.*—Near 137A; Under side: Near 137D.
*Young leaf, upper side.*—Near 138A; Under side: Near 137C.

Flower

Flower type: Single.
Flower shape: Flat and circular.
Flowering habit: Uniform.
Number of blossoms per branch: Between 4 and 6.
Inflorescence form: Pyramidal.
*Depth of fully expanded blossoms.*—Near 2 cm.
*Diameter of fully expanded blossoms.*—5–7 cm.
Phyllaries:
*Number.*—20–25.
*Color.*—Near 137B.
*Length.*—0.8–1.2 cm.
*Width.*—0.2–0.3 cm.
*Texture/appearance.*—Pubescent.
Pedicel length is more or less equal over all flowers and between 7 and 8 cm:
*Length.*—7–8 cm.
*Color.*—Near 137B.
*Surface.*—Pubescent.
*Habit.*—Slightly undulating.
*Strength.*—Medium.
Ray florets:
*Form/shape.*—Reflexing 1.
*Texture/appearance.*—Matte.
*Number per flower.*—34–40.
*Length.*—2.5–4 cm; Width: 0.6–1 cm.
*Apex.*—Rounded some slightly dentate.
*Base.*—Tapered.
*Margin.*—Entire.
Disc florets:
*Form/shape.*—Cylindrical.
*Texture/appearance.*—Shiny.
*Number per flower.*—160–220.
*Length.*—0.4–0.6 cm; Width <0.1 cm.
*Diameter of disc.*—1–1.6 cm.
Fragrance: Faint.
Flower bud (at onset of color):
*Length.*—Near 0.8 cm.
*Diameter.*—Near 1 cm.
*Form/shape.*—Globular.
General flower color:
1. *Ray florets, upper side.*—Immature: Near 34A. Mature: Near 30A. Older/Fading: Near 30B.
2. *Ray florets, under side.*—Immature: Near 34B. Mature: Near 30B. Older/Fading: Near 30B.
3. *Disc florets.*—Immature: Near 151B. Mature: Near 7A. Older/Fading: Near 7A.
4. *Bud.*—Near 138B.

Flower progression with age: Flowers slightly fading from deep orange red bronze to orange bronze with age.

Reproductive Organs

Gynoecium: Present on both ray and disc florets.
*Pistil number on ray florets.*—34–40.
*Pistil number on disc florets.*—160–220.
*Stigma color.*—Near 6C.
*Stigma shape.*—Forked.
*Style color.*—Near 6C.
*Style length on ray florets.*—Near 0.5 cm.
*Style length on disc florets.*—Near 0.1 cm.
Androecium: Present on disc florets only.
*Stamen number.*—<5.
*Anther shape.*—Clubbed.

*Anther color.*—15B.

*Pollen quantity.*—None observed.

*Pollen color.*—None observed.

Fruit and seeds: None observed.

What is claimed is:

1. A new and distinct variety of Chrysanthemum plant, substantially as described and illustrated herein.

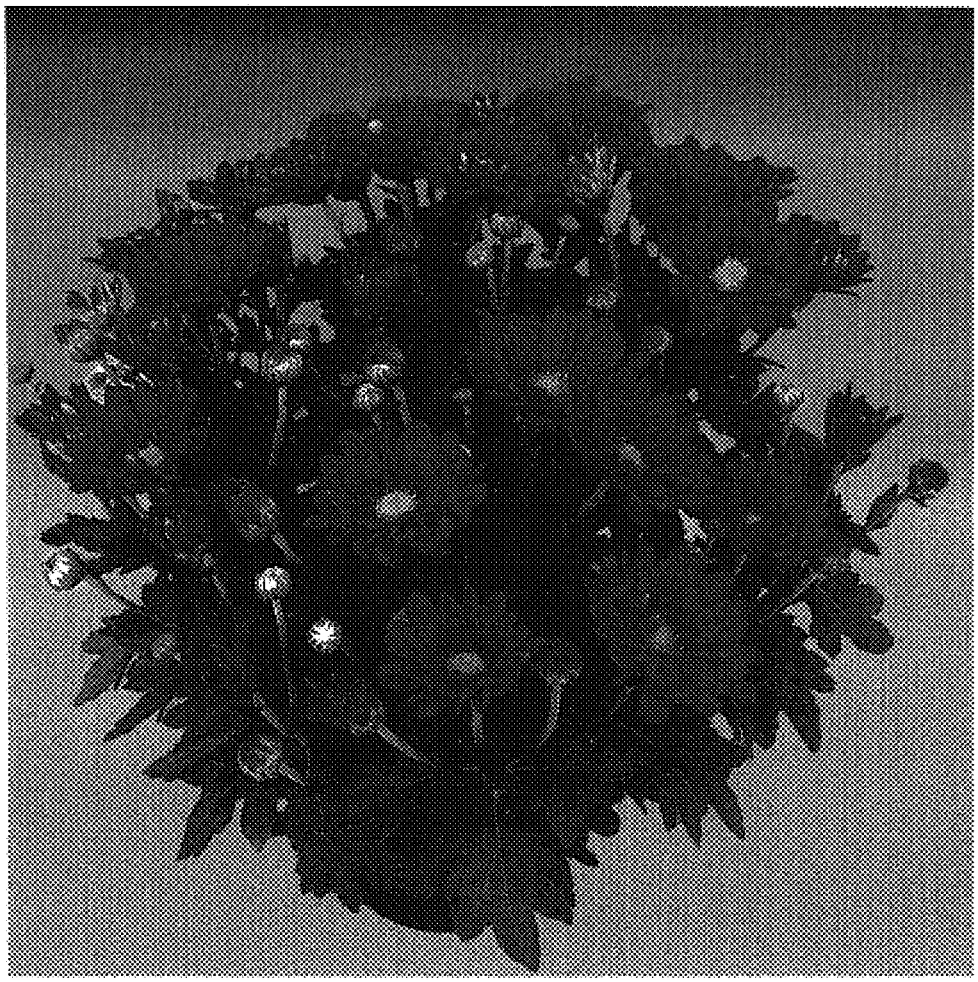

* * * * *